(12) United States Patent
Mito (10) Patent No.: US 9,453,825 B2
(45) Date of Patent: Sep. 27, 2016

(54) CHROMATOGRAM PEAK PURITY DETERMINATION APPARATUS

(75) Inventor: Yasuhiro Mito, Kyotanabe (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 998 days.

(21) Appl. No.: 13/603,174

(22) Filed: Sep. 4, 2012

(65) Prior Publication Data

US 2014/0067283 A1   Mar. 6, 2014

(51) Int. Cl.
*G01N 30/86* (2006.01)

(52) U.S. Cl.
CPC ...... *G01N 30/8634* (2013.01); *G01N 30/8693* (2013.01)

(58) Field of Classification Search
None
See application file for complete search history.

(56) References Cited

U.S. PATENT DOCUMENTS 6,393,368 B1 *  5/2002  Ito .................. G01N 30/8624
                                                    702/22

* cited by examiner

*Primary Examiner* — Aditya Bhat
(74) *Attorney, Agent, or Firm* — Morgan, Lewis & Bockius LLP (57) ABSTRACT

An apparatus and a method for chromatogram peak purity determination are provided, where the chromatogram's dimensions consist of retention time, wavelength and absorbance. The apparatus or method accumulates, at each retention time, absorbance in the wavelength direction for all or a part of a wavelength range in a predetermined retention time range; extracts a plurality of groups where, for each group, the absorbance accumulation value is the same for one point on a rising slope and one point on a falling slope regarding a peak that exists on a chromatogram that is prepared based on a 2-dimensional data whose dimensions are absorbance accumulation value and retention time; calculates similarities between absorption spectrum pattern at one point on the rising slope and at one point on the falling slope for each group; and determines from the plurality of groups, whether the peak consists of a single component based on similarity.

6 Claims, 5 Drawing Sheets

CHROMATOGRAM PEAK PURITY DETERMINATION APPARATUS

FIELD OF THE INVENTION

The present invention relates to a data processing apparatus for processing data that is obtained from liquid chromatograph and the like and relates, in particular, to an apparatus for determining the purity of peaks that appear in chromatograms obtained from chromatographs that use multi-channel detectors such as photodiode array detectors.

BACKGROUND OF THE INVENTION

When a specimen is analyzed with a liquid chromatograph or the like, peaks that correspond to components that are included in the analyzed specimen appear on the chromatogram. However, a peak that appears as a single shape on a chromatogram is not necessary created by a single component and may in fact represent a plurality of components that have not been sufficiently separated in a liquid chromatograph column. This has heretofore led to the use of chromatogram peak purity determination apparatus to determine whether or not a peak in a chromatogram represents a single component.

Non-Patent Literature 1 discloses peak purity determination methods that are used with chromatograms that are obtained with liquid chromatographs that use photodiode array (PDA) detectors. Using a PDA detector provides three-dimensional data consisting of wavelength, retention time and signal strength. Non-Patent Literature 1 describes two peak purity determination methods.

With the first method, the determination of the purity of a peak on a chromatogram involves comparing the absorption spectrum pattern at three points—at the peak top, peak rising slope and peak falling slope—and determining the degree of match between the spectrum pattern at the peak top and the spectrum pattern at the peak rising slope, and the degree of match between spectrum pattern at the peak top and the spectrum pattern at the peak falling slope. (The method for determining the degree of match between spectrum patterns is described in detail in Patent Literature 1.) The average value of the two degrees of match is then determined and compared against a predefined threshold value. Depending on whether or not the average value is greater than the predefined threshold value, determination is made as to whether or not there is a single peak.

With the other method, a "threshold value" and "similarity" between the absorption spectrum at the peak top and each absorption spectrum from the peak starting time to the peak ending time are calculated. The value of "similarity—threshold value" is then plotted on a time axis. Whether or not the value of "similarity—threshold value" becomes a negative value during the time that the particular peak is present is used to determine the purity of a peak (Non-Patent Literature 2).

Patent Literature 1: Examined Patent Application Publication No. 7-74761

NON-PATENT LITERATURE

Non-Patent Literature 1: Yasuhiro Mito, Mitsuo Kitaoka, "Photodiode Array UV—VIS Detector SPD—M6A for Shimadzu HPLC Use," *Shimadzu Hyouron*, Vol. 46, No. 1, July 1989, pp. 21-28

Non-Patent Literature 2: "LC Workstation CLASS-VP Ver 6.1 Instruction Manual," Shimadzu Corporation, April 2001, pp. 9-40 through 9-41

SUMMARY OF THE INVENTION

With absorption spectrophotometric detector used with liquid chromatographs, the effect of stray light causes a lack of linearity in concentration versus absorbance in high concentration regions. For this reason, spectrum patterns may not agree completely even for the same component between a low-concentration spectrum and a high concentration spectrum. This means that a risk with the two afore-described methods is that if the peak top has a high concentration, the purity may be judged as being low even if the peak may contain only one component. Also, the effects of reduced linearity become particularly pronounced when operating in a low-wavelength range (190 nm through 220 nm) where the energy of the light-source lamp is low, and this can cause distortion of the spectrums, which can also result in a single-component peak to be judged as low in purity.

The present invention was made in light of the afore-described problems, and it is the object of the present invention to provide a chromatogram peak purity determination apparatus wherein the accuracy of peak purity determination is maintained even in high concentration regions.

A first mode of the present invention that was made for solving the afore-described problem is a chromatogram peak purity determination apparatus for use in a data processing apparatus for chromatographs, which use photodiode array detector as a detector for collecting 3-dimensional data whose dimensions consist of retention time, wavelength and absorbance, for determining the purity of a peak that exists in a chromatogram that is prepared based on the 3-dimensional data and includes:

a) an absorbance accumulation means for accumulating, at each retention time, absorbance in the wavelength direction for all or a part of a wavelength range in a predetermined retention time range;

b) an equal absorbance accumulation value group extracting means for extracting a plurality of groups wherein, for each group, the absorbance accumulation value is the same for one point on a rising slope and one point on a falling slope with respect to a peak that exists on a chromatogram that is prepared based on a 2-dimensional data whose dimensions are the absorbance accumulation value and retention time;

c) a similarity calculation means for calculating similarity between absorption spectrum pattern at one point on the rising slope and absorption spectrum pattern at one point on the falling slope for each group that is extracted by the equal absorbance accumulation value group extracting means; and d) a determination means for determining, with respect to the plurality of groups that are extracted by the absorbance accumulation value group extracting means, whether or not the peak consists of a single component based on similarity that is calculated by the similarity calculation means.

Here, the chromatograph can be either a liquid chromatograph or a gas chromatograph. Also, the phrase "predetermined retention time range" refers to a time range that is set in advance as a portion of the absorbance detection time and must contain, at least the time range from peak starting time to peak ending time.

A chromatogram peak purity determination apparatus according to a second mode of the present invention is the chromatogram peak purity determination apparatus according to the first mode wherein, for a retention time range ranging from a peak starting time to a peak ending time for a peak in a 3-dimensional chromatogram, the absorbance accumulation means accumulates, at each retention time, absorbance in the wavelength direction for all or a part of the wavelength range.

A chromatogram peak purity determination apparatus according to a third mode of the present invention is the chromatogram peak purity determination apparatus according to the first or second mode wherein the similarity calculation means represents the absorption spectrum pattern of one point on a rising slope and the absorption spectrum pattern of one point on a falling slope using vectors whose elements are absorbance at each wavelength and the cosine of the included angle formed by the vectors is used to calculate similarity.

A chromatogram peak purity determination apparatus according to a fourth mode of the present invention is the chromatogram peak purity determination apparatus according to the third mode wherein the determination means makes a determination by comparing a determination value and an average value of the cosines of a plurality of groups.

A chromatogram peak purity determination apparatus according to a fifth mode of the present invention is the chromatogram peak purity determination apparatus according to the third mode wherein the determination means makes a determination by comparing a determination value and variance of the cosines of a plurality of groups.

A chromatogram peak purity determination method according to a sixth mode of the present invention is a chromatogram peak purity determination method for use in a data processing apparatus for chromatographs, which use photodiode array detector as a detector for collecting 3-dimensional data whose dimensions consist of retention time, wavelength and absorbance, for determining the purity of a peak that exists in a chromatogram that is prepared based on said 3-dimensional data and includes:

an absorbance accumulation step for accumulating, at each retention time, absorbance in the wavelength direction for all or a part of a wavelength range in a predetermined retention time range;

an equal absorbance accumulation value group extracting step for extracting a plurality of groups wherein, for each group, the absorbance accumulation value is the same for one point on a rising slope and one point on a falling slope with respect to a peak that exists on a chromatogram that is prepared based on a 2-dimensional data whose dimensions are retention time and absorbance accumulation value that was accumulated by said absorbance accumulation step;

a similarity calculation step for calculating similarity between absorption spectrum pattern at one point on the rising slope and absorption spectrum pattern at one point on the falling slope for each group that is extracted by the equal absorbance accumulation value group extracting means; and a determination step for determining, with respect to the plurality of groups that are extracted by the absorbance accumulation value group extracting step, whether or not the peak consists of a single component based on similarity that is calculated by the similarity calculation step.

With a chromatogram peak purity determination apparatus according to the invention of the present application, absorbance is accumulated in the wavelength direction for each retention time. In 2-dimensional chromatograms whose dimensions are the calculated absorbance accumulation value and retention time, a plurality of spectrum groups whose absorbance accumulation values are the same is detected, and similarity of the spectrum pattern is calculated for each group to determine the purity of the peak.

Reference is made to the method described in Patent Literature 1 for the calculation of similarity of spectrum patterns. Patent Literature 1 discloses an approach for calculating similarity that is vector-based wherein absorption spectrums are represented as a set of discrete absorbance data that is detected for a series of wavelengths which are then vectorized.

Specifically, an absorption spectrum is represented as $\vec{S}=(a(\lambda 1), a(\lambda 2), a(\lambda 3) \ldots, a(\lambda n))$. The symbol "$\rightarrow$" identifies a vector. The notation "$a(\lambda n)$" means absorbance at wavelength $\lambda n$.

If 2 absorption spectrums are represented by vectors as described above and if the spectrums consist of identical components, their representation as vectors as afore-described will result in the spectrum patterns to be the same, and the vectorized spectrums will be oriented in the same direction. If similarity is defined by the value of the cosine of the included angle $\theta$ formed by the two vectorized spectrums, the value of $\theta$ of the included angle of the two vectorized spectrums will be 0, and the cosine value $\cos\theta$ will be 1 for two vectors that are identical. Stated otherwise, the closer the value of similarity to 1, the more similar the spectrum patterns.

Based on the afore-described thinking, with the invention of the present application, a plurality of spectrum group whose absorbance accumulation value is the same is extracted from the rising slope and the falling slope for any given peak, and similarity is examined based on the vectorized representation of the spectrum for each spectrum group.

Figure 1:
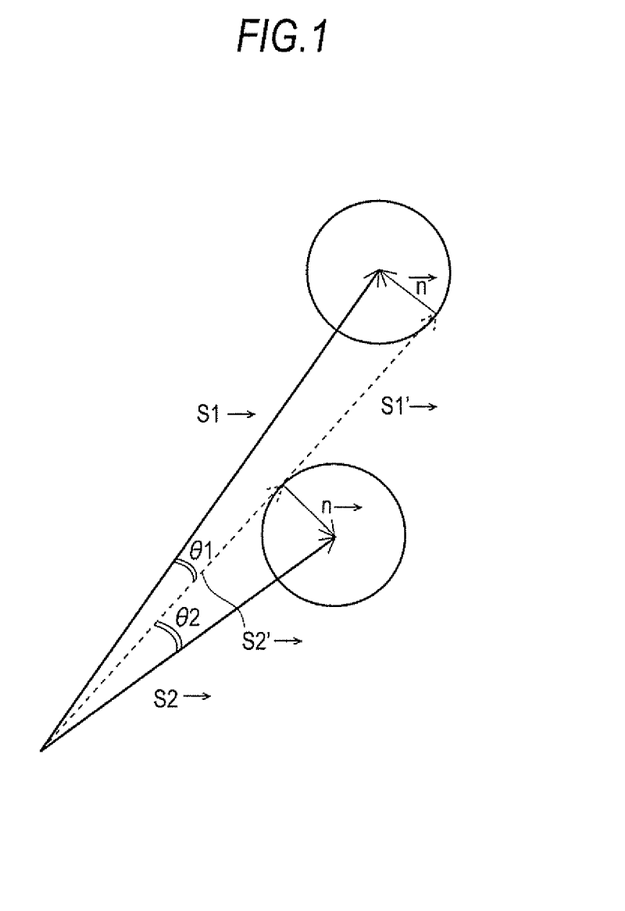
FIG. 1 shows a figure used for explaining the spectrum pattern similarity determination method according to the present invention.

The determination of peak purity based on similarity is performed by comparing the average value of similarity to a determination value. Here, the term "determination value" (K) refers to a maximum allowed value for determining that spectrum patterns are similar, taking into account the effects of detection noise of the detector and other factors. Assume that the effect of noise has shifted vectors that are actually the same by $\vec{n}$, causing $\vec{S1}$ to be displaced from the true vector $\vec{S1'}$ by $\theta 1$ and $\vec{S2}$ to be displaced from the true vector $\vec{S2'}$ by $\theta 2$ (FIG. 1). The match between the true vectors $\vec{S1'}$ and $\vec{S2'}$ is achieved within a range of a maximum of $\theta 1+\theta 2$ of the included angle. This means that the determination value (K), which is the maximum allowed range of similarity between vectors, is $\cos(\theta 1+\theta 2)$. Here, K is calculated using equation 1:

$$K = \cos(\theta 1 + \theta 2) \hspace{2cm} \text{Equation 1}$$
$$= \cos\theta 1 \cos\theta 2 - \sin\theta 1 \sin\theta 2$$
$$= \sqrt{\left(1 - \frac{|\vec{n}|^2}{|\vec{S1}|^2}\right)\left(1 - \frac{|\vec{n}|^2}{|\vec{S2}|^2}\right)} - \frac{|\vec{n}|^2}{|\vec{S1}||\vec{S2}|}$$

In this way, with a chromatogram peak purity determination apparatus according to the present invention, peak purity is determined by comparing the similarity of spectrum patterns using spectrum groups having the same absorbance accumulation value. Groups whose value of absorbance accumulated in the wavelength direction is the same are inferred to have a substantially equal concentration of specimens that are detected during their respective retention time. Hence, this means that with the present invention, similarity is compared between spectrum groups whose concentration is substantially equal. In this way, because similarity of spectrum is not compared between a high-concentration region and a low-concentration region, the effects of a lack of linearity in the high concentration region is avoided, and the accuracy of peak purity determination is maintained even in high concentration regions.

DETAILED DESCRIPTION OF THE INVENTION

A liquid chromatograph that is one embodiment of a liquid chromatograph that uses a peak purity determination apparatus according to the present invention is described next with reference to FIG. 2 through FIG. 5.

Embodiments

Figure 2:
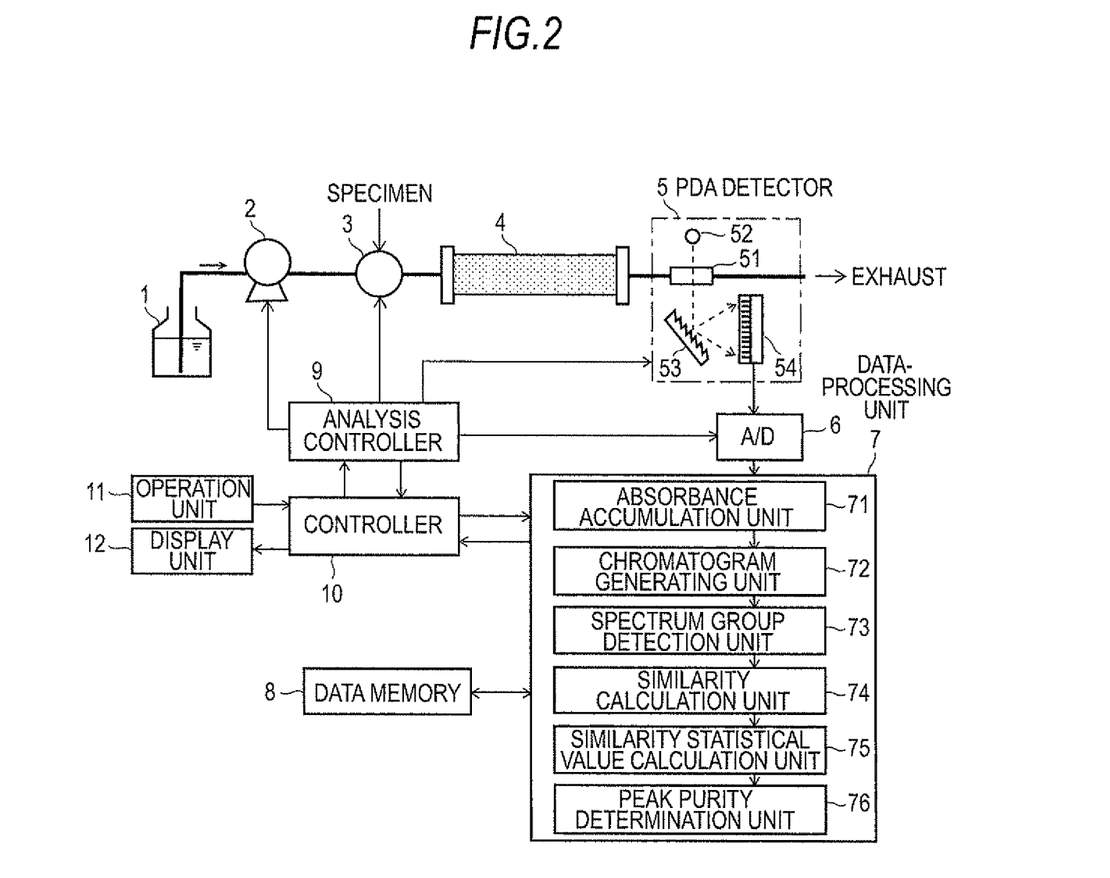
FIG. 2 shows the major components of a liquid chromatograph that is one embodiment of a chromatograph that uses a chromatogram peak purity determination apparatus according to the present invention.

FIG. 2 shows the major components of a liquid chromatograph that uses a chromatogram peak purity determination apparatus according to the present embodiment. With this liquid chromatograph, liquid feed pump 2 draws in a mobile phase that is contained in mobile phase container 1 and feeds the mobile phase at a substantially constant flow rate to column 4 via injector 3. At predetermined timings, injector 3 injects into the mobile phase a specimen that was readied in advance. The injected liquid specimen is carried by the mobile phase into column 4. As the liquid specimen passes through column 4, various specimen components that are included in the liquid specimen are separated and elute out of column 4 with a time deviation.

Located at the outlet of column 4 is PDA detector 5 for detecting the specimen components that are contained in the liquid that elutes out from column 4. PDA detector 5 includes: transparent flow cell 51 through which the eluted liquid flows; light source 52; spectrometer 53 for separating by wavelength the light that passes through flow cell 51; and PDA device 54 for detecting the wavelength-separated light nearly simultaneously.

The detection signals from PDA detector 5 are converted to digital signals by A/D converter 6 and are input to data-processing unit 7 and are temporarily stored in data memory 8. The data that is stored in data memory 8 is processed in various ways by data-processing unit 7 as further described below. In particular, to perform the peak purity determination process further described below, the data-processing unit 7 includes the following functional blocks: absorbance accumulation means 71; chromatogram generating unit 72; spectrum group detection unit 73; similarity calculation means 74; similarity statistical value calculation unit 75; and peak purity determination unit 76.

Based on instructions from controller 10, analysis controller 9 controls various units such as liquid feed pump 2. Connected to controller 10, which primarily plays a role in the user interface, are an operation unit 11 such as mouse and keyboard that are operated by the user and a display unit 12 for displaying measurement results and the like. The entirety or a part of the functions of the analysis controller 9, controller 10 and data-processing unit 7 can be implemented by a configuration featuring a general-purpose personal computer serving as hardware and dedicated control/processing software that is installed in advance on the personal computer.

Because PDA detector 5 is capable of simultaneously detecting a plurality of wavelengths without performing wavelength scanning, absorption spectrum data over a predetermined wavelength range can be obtained with a predetermined time interval starting with when the specimen was injected into the mobile phase by injector 3. This means that, with this liquid chromatograph, 3-dimensional data such as that shown in FIG. 3(a) whose 3 dimensions are time Ti, wavelength $\lambda j$ and signal strength Aij can be obtained. When liquid chromatography is performed on a specimen under the control of analysis controller 9, 3-dimensional data from analysis starting time (specimen injection timing) to the analysis ending time is stored in data memory 8.

Figure 3:
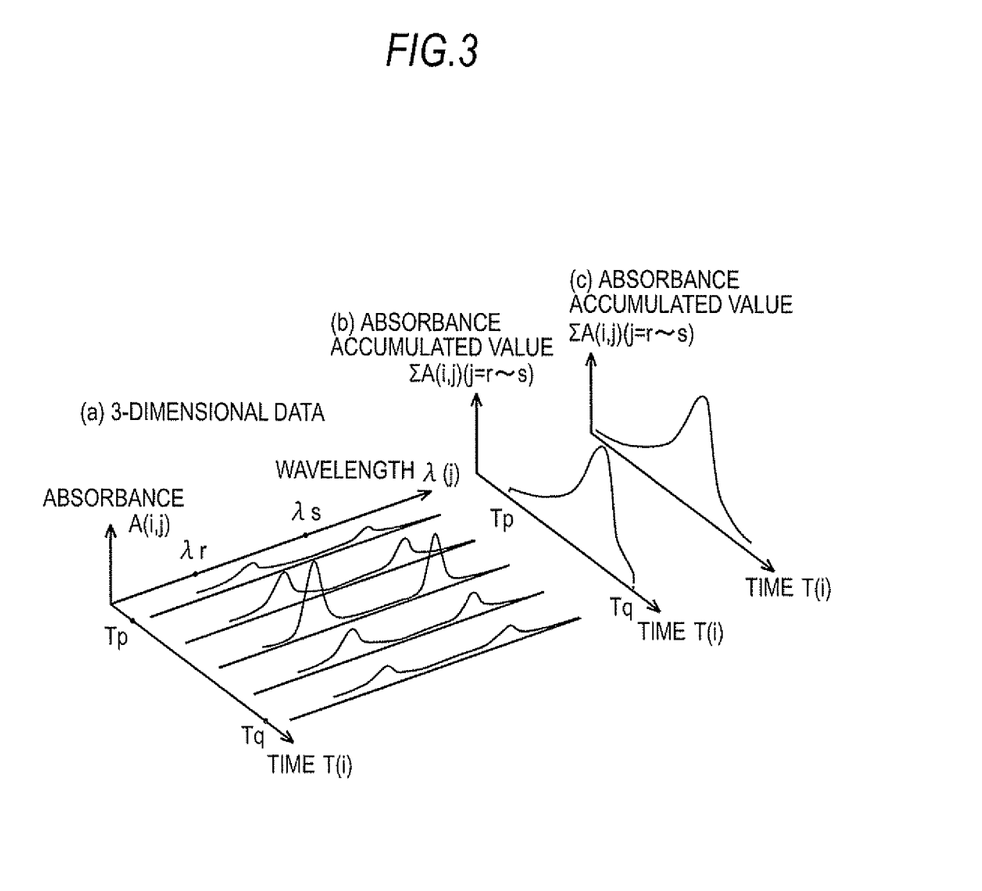
FIG. 3(a) shows a graph of 3-dimensional data that is obtained with a liquid chromatograph of the present embodiment.
FIG. 3(b) shows a chromatogram where absorbance accumulation value in the wavelength direction is plotted in the time direction for a predetermined time range.
FIG. 3(c) shows a chromatogram where absorbance accumulation value in the wavelength direction is plotted in the time direction from the start of a peak to the end of the peak.
Figure 4:
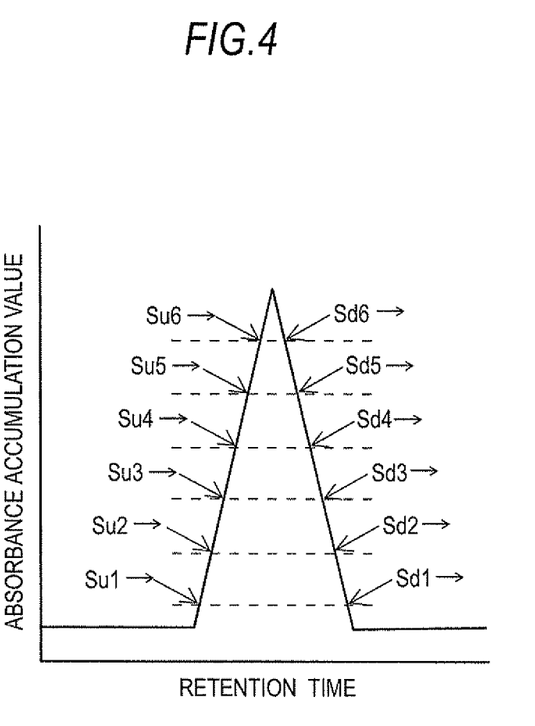
FIG. 4 is used for explaining the method for dividing a chromatogram peak that is discussed with the present embodiment.

The typical peak purity determination process that centers on data-processing unit 7 and is performed by a liquid chromatograph according to the present embodiment is described next with reference to FIG. 3 and FIG. 4.

Prior to performing specimen analysis with a liquid chromatograph, the user uses operation unit 11 to set the retention time range and the wavelength where the peak for the specimen is expected to be detected. When the analysis is completed, the absorbance accumulation means 71 reads the 3-dimensional data from data memory 8 in accordance with the user's instructions entered from operation unit 11 and accumulates the absorbance at each retention time over the retention time range (Tp through Tq) set in advance for the wavelength range ($\lambda r$ through $\lambda s$) set in advance. The accumulation of absorbance is performed according to:

$$A\text{total}(i) = \Sigma A(i,j)(j = r \text{ through } s)$$

With the present embodiment, the range of wavelength and retention time was set in advance as the absorbance accumulation range. It is also possible to display a 3-dimensional chromatogram on a display screen and for the user to operate a mouse and the like to specify the retention time range and the wavelength range to be used for accumulating the absorbance.

Chromatogram generating unit 72 displays on the screen of display unit 12 a 2-dimensional chromatogram where absorbance accumulation value Atotal(i) calculated by absorbance accumulation means 71 is plotted in the retention time Ti (i=p through q) direction (see FIG. 3(b)).

The spectrum group detection unit 73 divides the peak top height in the 2-dimensional chromatogram (FIG. 3(b)) generated by the chromatogram generating unit 72 into a plurality of equal segments and determines equal absorbance groups where one point on the rising slope and one point on the falling slope have the same absorbance accumulation value. With the present embodiment, the peak top height is divided into 7 equal segments, and 6 equal absorbance accumulation value groups are obtained (see FIG. 4). Here, Su1→ through Su6→ and Sd1→ through Sd6→ represent the spectrum at each point as vectors. For example, Su1→ represents (A(λr), . . . A(λs)).

For each equal absorbance group that was detected by spectrum group detection unit 73, similarity calculation means 74 calculates spectrum similarity R. For each point on the rising slope and the falling slope of the peak, the respective spectrums are vectorized, and similarity is defined as the cosine value cos θ of included angle θ formed by the vectors. Specifically, similarity is calculated using the following equation (equation (2)).

$$R = \cos\theta = Su_x\rightarrow \cdot Sd_x\rightarrow / |Su_x\rightarrow|\cdot|Sd_x\rightarrow| \qquad \text{Equation 2}$$

Similarity statistical value calculation unit 75 uses spectrum similarity R for each equal absorbance group calculated by similarity calculation means 74 to calculate the average similarity value $R_{ave}$ for all groups. The maximum allowed range of similarity for determining whether or not spectrums are identical, that is, the determination value, is also calculated. Here, the determination value K is represented by:

$$K = \sqrt{\left(1 - \frac{|n\rightarrow|^2}{|Su_x\rightarrow|^2}\right)\left(1 - \frac{|n\rightarrow|^2}{|Sd_x\rightarrow|^2}\right)} - \frac{|n\rightarrow|^2}{|Su_x\rightarrow||Sd_x\rightarrow|} \qquad \text{Equation 3}$$

Here, n→ is the vectorized representation of the shift caused by noise.

The peak purity determination unit 76 uses the determination value and the average similarity value calculated by similarity statistical value calculation unit 75 to determine whether or not the peak in question consists of a single component. Specifically, peak purity determination unit 76 compares the average value $K_{ave}$ of determination values K against the average value $R_{ave}$ of similarity R calculated by the similarity statistical value calculation unit 75. If $R_{ave} \geq K_{ave}$, a determination is made that the spectrums of the equal absorbance group are identical. The fact that the spectrums of the equal absorbance group are identical means that the rising slope and the falling slope of the peak are identical and that the peak consists of a single component.

The invention of the present application was made in light of the fact that linearity of concentration versus absorbance drops in high-concentration regions. The effect of the difference in concentration on spectrum pattern was then studied.

Figure 5:
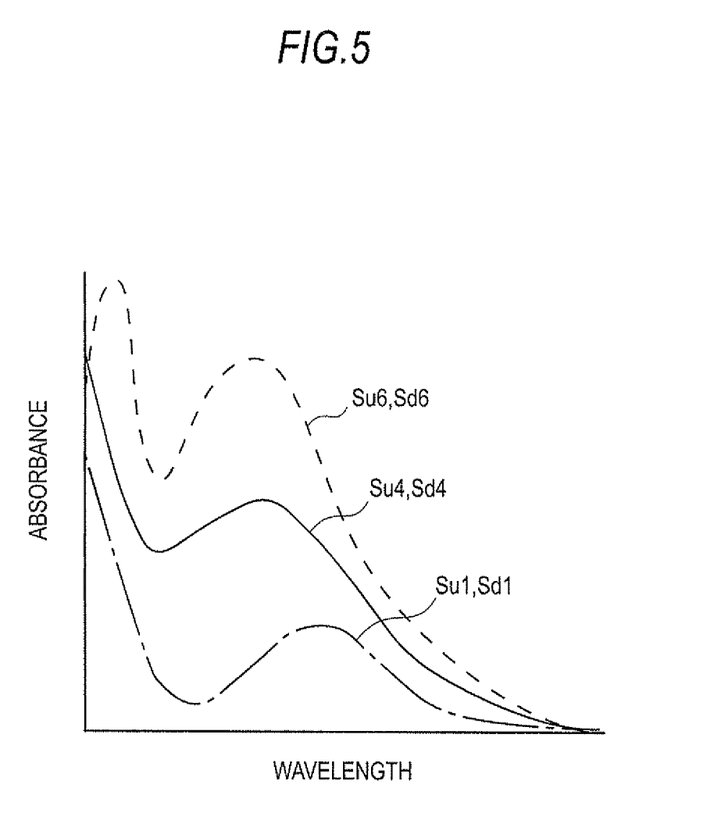
FIG. 5 shows a plot in the wavelength direction for spectrums in a chromatogram peak that was discussed with the present embodiment.

FIG. 5 shows spectrums Su1, Su4, Su6, Sd6, Sd4 and Sd1 of the peak plotted in the wavelength direction that was studied for the present embodiment.

FIG. 5 shows that the spectrum patterns are greatly different between Su1 and Sd1 which belong in the low-concentration region, Su6 and Sd6 which belong to the high-concentration region, and Su4 and Sd4 which belong to the intermediate-concentration region. The spectrum patterns match each other completely between Su1 and Sd1, between Su4 and Sd4, and between Su6 and Sd6. In this way, the effect of concentration on spectrum pattern is quite significant. In regions of equal concentration, the spectrum patterns match each other completely. Because of these facts, it is believed that a chromatogram peak purity determination apparatus according to the invention of the present application is believed to achieve a peak purity determination with higher accuracy than previous determination apparatuses.

The present invention is not limited to the afore-described embodiment and various modifications are possible without deviating from the scope of the invention. For example, even though, with the afore-described embodiment, absorbance was accumulated over a retention time range that was set in advance, it is acceptable to accumulate absorbance from the start to the end of the target peak (see FIG. 3(*c*)). It is also acceptable to accumulate absorbance from before the peak starting time and beyond the peak ending time. To accumulate absorbance from the start to end of a peak, the user uses operation unit 11 to specify the starting timing and the ending timing of the target peak whose peak purity is to be determined. In lieu of the user manually specifying the peak starting timing and the ending timing, it is also acceptable to configure so that the peak starting timing and the ending timing are automatically determined for a target peak that is identified by the user. It is also acceptable to configure so that the peaks themselves are automatically detected and for the starting time and ending time to be automatically set for all detected peaks. The automatic detection of peaks or the starting and ending timings of a peak can be performed using conventional peak detection methods.

Furthermore, with the afore-described embodiment, absorbance was accumulated over the entire wavelength falling within the range of λr through λs that was set in advance. However, it is also acceptable to accumulate absorbance that is detected just for a plurality of specific wavelengths (i.e., to ignore some of the wavelengths in performing the calculations). As an extreme example, it is acceptable to use a configuration wherein absorbance is accumulated just for 2 wavelengths.

With the present embodiment, in detecting a plurality of equal absorbance accumulation value groups from one peak on a chromatogram, the peak top height was divided into 7 equal parts. However, the number of divisions of 7 is not a limitation, and the fact the peak top height was divided into equal parts is not a limitation either. To detect the equal absorbance accumulation value groups, the fact that a 2-dimensional chromatogram was prepared using accumulated values is not a limitation. Instead, equal absorbance accumulation value groups can be detected solely based on calculations.

Furthermore, even though, with the present embodiment, peak purity was determined based on a comparison of similarity average value $R_{ave}$ and determination value average value $K_{ave}$, which was determined by calculation, it is also acceptable to set the determination value based on experiments.

Even though, with the present embodiment, average similarity value was used as the basis for the determination of peak purity, peak purity can also be determined using variance or standard deviation of similarity. The calculation of variance or standard deviation of similarity is performed by similarity statistical value calculation unit 75. If the target peak consists of a single component, similarity R(=cos θ) of the equal absorbance group in the rising slope and the falling slope will be close to 1. Hence, the variance or standard deviation of similarity among all equal absorbance groups will be a small value. The peak purity determination unit 76 determines the purity of a target peak by comparing the variance or standard deviation against a threshold value that is set in advance by the user.

As a variation, instead of accumulating absorbance over a predetermined wavelength range, it is acceptable to generate a 2-dimensional chromatogram that plots signal strength at one specific wavelength in the time direction and to extract equal absorbance groups from the chromatogram for further examination.

LEGEND 1. mobile phase container
2. liquid feed pump
3. injector
4. column
5. PDA detector
51. flow cell
52. light source
53. spectrometer
54. FDA device
6. A/D converter
7. data-processing unit
71. absorbance accumulation means
72. chromatogram generating unit
73. spectrum group detection unit
74. similarity calculation means
75. similarity statistical value calculation unit
76. peak purity determination unit
8. data memory
9. analysis controller
10. controller
11. operation unit
12. display unit

What is claimed is:

1. A chromatogram peak purity determination apparatus for use in a data processing apparatus for chromatographs, which use photodiode array detector as a detector for collecting 3-dimensional data whose dimensions consist of retention time, wavelength and absorbance, for determining the purity of a peak that exists in a chromatogram that is prepared based on said 3-dimensional data and comprising:
   a) an absorbance accumulation means for accumulating, at each retention time, absorbance in the wavelength direction for all or a part of a wavelength range in a predetermined retention time range;
   b) an equal absorbance accumulation value group extracting means for extracting a plurality of groups wherein, for each group, the absorbance accumulation value is the same for one point on a rising slope and one point on a falling slope with respect to a peak that exists on a chromatogram that is prepared based on a 2-dimensional data whose dimensions are said absorbance accumulation value and retention time;
   c) a similarity calculation means for calculating similarity between absorption spectrum pattern at one point on the rising slope and absorption spectrum pattern at one point on the falling slope for each group that is extracted by said equal absorbance accumulation value group extracting means; and
   d) a determination means for determining, with respect to the plurality of groups that are extracted by said absorbance accumulation value group extracting means, whether or not said peak consists of a single component based on similarity that is calculated by said similarity calculation means.

2. The chromatogram peak purity determination apparatus according to claim 1 wherein, for a retention time range ranging from a peak starting time to a peak ending time for a peak in a 3-dimensional chromatogram, said absorbance accumulation means accumulates, at each retention time, absorbance in the wavelength direction for all or a part of the wavelength range.

3. The chromatogram peak purity determination apparatus according to claim 1 wherein said similarity calculation means represents the absorption spectrum pattern of one point on a rising slope and the absorption spectrum pattern of one point on a falling slope using vectors whose elements are absorbance at each wavelength and the cosine of the included angle formed by said vectors is used to calculate similarity.

4. The chromatogram peak purity determination apparatus according to claim 3 wherein said determination means makes a determination by comparing a determination value and an average value of the cosines of a plurality of groups.

5. The chromatogram peak purity determination apparatus according to claim 3 wherein said determination means makes a determination by comparing a determination value and variance of the cosines of a plurality of groups.

6. A chromatogram peak purity determination method for use in a data processing apparatus for chromatographs, which use photodiode array detector as a detector for collecting 3-dimensional data whose dimensions consist of retention time, wavelength and absorbance, for determining the purity of a peak that exists in a chromatogram that is prepared based on said 3-dimensional data and comprising:
   an absorbance accumulation step for accumulating, at each retention time, absorbance in the wavelength direction for all or a part of a wavelength range in a predetermined retention time range;
   an equal absorbance accumulation value group extracting step for extracting a plurality of groups wherein, for each group, the absorbance accumulation value is the same for one point on a rising slope and one point on a falling slope with respect to a peak that exists on a chromatogram that is prepared based on a 2-dimensional data whose dimensions are retention time and absorbance accumulation value that was accumulated by said absorbance accumulation step;
   a similarity calculation step for calculating similarity between absorption spectrum pattern at one point on the rising slope and absorption spectrum pattern at one point on the falling slope for each group that is extracted by said equal absorbance accumulation value group extracting step; and
   a determination step for determining, with respect to the plurality of groups that are extracted by said absorbance accumulation value group extracting step, whether or not said peak consists of a single component based on similarity that is calculated by said similarity calculation step.

* * * * *